United States Patent
Jeraj et al.

(10) Patent No.: US 9,603,567 B2
(45) Date of Patent: *Mar. 28, 2017

(54) SYSTEM AND METHOD FOR EVALUATION OF DISEASE BURDEN

(71) Applicant: Wisconsin Alumni Research Foundation, Madison, WI (US)

(72) Inventors: Robert Jeraj, Madison, WI (US); Glenn Liu, Waunakee, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/886,835

(22) Filed: Oct. 19, 2015

(65) Prior Publication Data

US 2016/0100795 A1    Apr. 14, 2016

Related U.S. Application Data

(63) Continuation of application No. 13/839,339, filed on Mar. 15, 2013, now Pat. No. 9,161,720.

(51) Int. Cl.

| A61B 5/05 | (2006.01) |
|---|---|
| A61B 5/00 | (2006.01) |
| A61B 5/055 | (2006.01) |
| A61B 6/03 | (2006.01) |
| A61B 6/00 | (2006.01) |
| A61B 6/12 | (2006.01) |

(Continued)

(52) U.S. Cl.
CPC .......... *A61B 5/4848* (2013.01); *A61B 5/0035* (2013.01); *A61B 5/055* (2013.01); *A61B 5/7275* (2013.01); *A61B 6/032* (2013.01); *A61B 6/037* (2013.01); *A61B 6/12* (2013.01); *A61B 6/461* (2013.01); *A61B 8/48* (2013.01); *A61B 8/5223* (2013.01); *G06T 7/0012* (2013.01); *G06T 7/0083* (2013.01); *A61B 5/742* (2013.01); *A61B 6/469* (2013.01); *A61B 6/505* (2013.01); *G06T 2207/10081* (2013.01); *G06T 2207/10088* (2013.01); *G06T 2207/10104* (2013.01); *G06T 2207/10108* (2013.01); *G06T 2207/20036* (2013.01); *G06T 2207/20148* (2013.01); *G06T 2207/30096* (2013.01)

(58) Field of Classification Search
CPC ....... A61B 5/4848; A61B 8/5223; A61B 8/48; A61B 6/12; A61B 5/0035; A61B 5/7275; A61B 5/055; A61B 6/032; G06T 7/0083; G06T 7/0012; G06T 2207/20148; G06T 2207/30096
USPC ................................. 600/407–480
See application file for complete search history.

(56) References Cited

U.S. PATENT DOCUMENTS

| 7,344,700 B2* | 3/2008 | Dalton | A61K 51/04 424/1.11 |
|---|---|---|---|
| 8,053,415 B2* | 11/2011 | Achilefu | A61K 47/48238 424/9.3 |

(Continued)

*Primary Examiner* — Sanjay Cattungal
(74) *Attorney, Agent, or Firm* — Boyle Fredrickson, S.C.

(57) ABSTRACT

A sensitive method of assessing treatment using molecular and anatomical imaging scans provides automatic tumor identification and quantification within anatomical zones based on treatment criteria. Absolute or comparative measures of tumors in pre- and/or post-scans are thereby isolated from other tissue to accentuate the progress of the treatment when multiple scattered disease lesions are present.

18 Claims, 4 Drawing Sheets

(51) Int. Cl.
*A61B 8/08* (2006.01)
*G06T 7/00* (2017.01)

(56) References Cited

U.S. PATENT DOCUMENTS

| | | | |
|---|---|---|---|
| 8,068,896 B2* | 11/2011 | Daghighian | A61B 6/037 |
| | | | 250/252.1 |
| 8,101,740 B2* | 1/2012 | Radu | A61K 51/0491 |
| | | | 536/24.3 |
| 8,338,366 B2* | 12/2012 | Lin | A61K 9/127 |
| | | | 424/1.69 |
| 2004/0052727 A1* | 3/2004 | Dalton | A61K 51/04 |
| | | | 424/1.11 |
| 2006/0251726 A1* | 11/2006 | Lin | A61K 9/127 |
| | | | 424/489 |
| 2008/0031815 A1* | 2/2008 | Chen | A61K 51/088 |
| | | | 424/9.1 |
| 2010/0010343 A1 | 1/2010 | Daghighian | A61B 6/037 |
| | | | 600/436 |
| 2010/0198061 A9* | 8/2010 | Daghighian | A61B 6/037 |
| | | | 600/436 |

* cited by examiner

SYSTEM AND METHOD FOR EVALUATION OF DISEASE BURDEN

CROSS REFERENCE TO RELATED APPLICATION

This application is a continuation of U.S. patent application Ser. No. 13/839,339, filed on Mar. 15, 2015, entitled "System and Method for Evaluation of Disease Burden." The entirety of the foregoing application is incorporated herein by reference.

STATEMENT REGARDING FEDERALLY SPONSORED RESEARCH OR DEVELOPMENT

This invention was made with government support under CA014520 and CA062491 awarded by the National Institute of Health. The government has certain rights in the invention.

BACKGROUND OF THE INVENTION

The present invention relates to techniques for assessing cancer treatment and in particular for a computerized assessment system using PET/CT or other anatomical, functional and molecular imaging techniques.

The assessment of treatment response in cancer patients receiving therapy is essential for disease management and clinical evaluation of therapy. Computed tomography (CT) is widely used to monitor cancer treatment by measuring changes in the diameters of the particular rumor lesions, for example, under the RECIST (Response Evaluation Criteria in Solid Tumors) guidelines. Such evaluations are subject to errors associated with the simplified characterization of a single dimension of a tumor, measurement of small tumors, or measurement of tumor size when tumor tissue is replaced with necrotic or fibrotic tissue. Often a particular tumor will not be representative of the disease as a whole. For these reasons, con elation between and similar measurements and clinical outcome is often weak.

Improved assessment of the efficacy of cancer treatments may be obtained by metabolic imaging of a type that can distinguish between necrotic and fibrotic tissue or healthy tissue and tumor tissue. One such imaging system is positron emission tomography (PET) that can distinguish among different types of tissue based on different uptake of a radioactive tracer compound targeted to a tumor. PET imaging may be used instead of or in addition to CT imaging to characterize particular tumors during treatment with improved result. The tumors visualized by PET may be manually identified, for example, by a physician drawing a region of interest (ROI) around the tumor and then measuring dimensions of the active portions of the tumor identified by the PET imaging The present inventors have demonstrated a significant improvement over conventional methods by using advanced PET-based analysis for early assessment of leukemia treatment efficacy. In this system bone marrow is automatically isolated from the combined PET/CT dataset and evaluated, in one example, based on standardized uptake values (SUV). The cortical bone surrounding the bone marrow tissue provides a sharp CT contrast with the neighboring tissue, its segmentation from the rest of the body helps isolating bone marrow tissue using a simple SUV threshold on the PET image (using 3'-Deoxy-3'-[$^{18}$F] Fluorothymidine (FLT) radiotracer). Measurement of bone marrow activity alone or in pre-treatment and post-treatment comparisons, as isolated from other tissue of the body, provides improved sensitivity and thus insight into the progress of the treatment.

PET-based assessment of cancer treatment treatments lamely concentrate on cancers involving solid tumors . . . . Such situations of localized disease allow ready characterization of the growth or shrinkage of disease tumors. Systemic diseases such as leukemia, lymphoma, or metastatic diseases in contrast, often present a diffuse or non-localized "continuous lesions" distributed in a large volume of body tissue. Focused measurement of such continuous lesions isolated from other tissue is difficult.

SUMMARY OF THE INVENTION

The present inventors have developed a technique for extending a molecular and functional imaging (e.g., PET, fMRI)-based automatic characterization of lesions to a variety of different cancer types including systemic cancer types involving a large volume of body tissue. The challenge of isolating multiple dispersed lesions from a large volume of surrounding uninvolved tissue, the latter such as may weaken the sensitivity of the tumor measurements, is addressed by an anatomical masking that focuses automatic lesion identification in likely tissue, on a case-by-case basis, as guided by information about the type of cancer and imaging materials. By using ex ante knowledge about the cancer and the molecular imaging agent uptake and retention distribution, automatic lesion identification on many dispersed lesions can be accomplished with a high degree of accuracy. Automatic measurement of many lesions allows an overview of the treatment that may be masked if only a few lesions are studied thereby providing a better understanding of disease progression.

In one embodiment, the invention provides a method of assessing cancer treatment comprising the steps of acquiring a scan of a molecular imaging uptake of tissue of the patient where the agent identifies tumor tissue, and processing the scan using an electronic computer. The computer executes a stored program to receive an input describing at least one of cancer type and agent type and uses that input to create a set of anatomical regions representing a subset of a region of the scan. Multiple tumor locations are identified within the anatomical regions based on agent uptake indicated by a molecular imaging (e.g., PET, SPECT) and an output indicating cancer progression based on measures of molecular imaging agent (e.g., FDG) uptake within the multiple tumor locations isolated from agent uptake outside of the multiple tumor locations.

It is thus a feature of at least one embodiment of the invention to effect a trade-off between providing a comprehensive evaluation of disease progression looking at many diffuse lesions while preserving a high degree of sensitivity by eliminating anatomical regions that may create false positive lesion activity (e.g., liver).

The method may output measures of molecular imaging agent uptake of individual subsets of the multiple tumor locations.

It is thus a feature of at least one embodiment of the invention to provide not only disease progression overview but additional information on individual tumors or groups of tumors that may provide useful clinical information (e.g., disease heterogeneity).

The measures of agent uptake of subsets may be divided in the output according to anatomical categories of tumor locations of the subsets.

It is thus a feature of at least one embodiment of the invention to broadly characterize the tumors and their measures with respect to body location to provide additional information about disease progression.

The method may further include a segmentation step defining boundaries around the tumor locations after the identification.

It is thus a feature of at least one embodiment of the invention to provide improved tumor area characterization by segmentation such as may affect tumor volume-based measures.

The method may include the step of acquiring multiple follow-up scans of the patient at a later time and repeating the above steps for the follow-up scans. In this case the output may indicate cancer progression or regression based on a comparison of measures of agent uptake within the multiple tumor locations isolated from agent uptake outside of the multiple tumor locations between scans.

It is thus a feature of at least one embodiment of the invention to permit longitudinal evaluation of single or multiple treatment stages.

The method may include the step of independently registering and matching measures of agent uptake between multiple tumors (lesions) of the scans.

It is thus a feature of at least one embodiment of the invention to provide increased accuracy in comparative analyses when tumors (lesions) may grow, shrink, fuse, split, appear, disappear migrate or shift with respect to each other.

The anatomical regions may be solid tumors or hematological disease (e.g., bone marrow) and the independent registration may match these lesions between corresponding anatomies scans rotated and shifted independently into alignment with each other.

It is thus a feature of at least one embodiment of the invention to provide a system well adapted to change patient anatomy which may shift during successive scans.

The output may include a graphic display of the tissue showing measures for different tumor locations color coded according to response between the scans.

It is thus a feature of at least one embodiment of the invention to provide a simple graphical representation showing disease progression.

The measures of the lesions may be selected from the group of comprehensive statistical evaluation of the scans (e.g., consisting of mean, max, peak, total, tumor heterogeneity measures, such as coefficient of variation, spatial statistics, lesion volume, lesion linear dimension, or other imaging features).

It is thus a feature of at least one embodiment of the invention to provide a system that works with a variety of well-understood lesion characterizations.

The scan of the method may be a combined molecular/anatomical imaging and the method may include the step of acquiring an anatomical scan (e.g., CT, MRI) of the tissue of the patient and processing the anatomical scan and the input to produce the set of anatomical regions of interest.

These particular objects and advantages may apply to only some embodiments failing within the claims and thus do not define the scope of the invention.

DETAILED DESCRIPTION OF A PREFERRED EMBODIMENT

System Hardware

Figure 1:
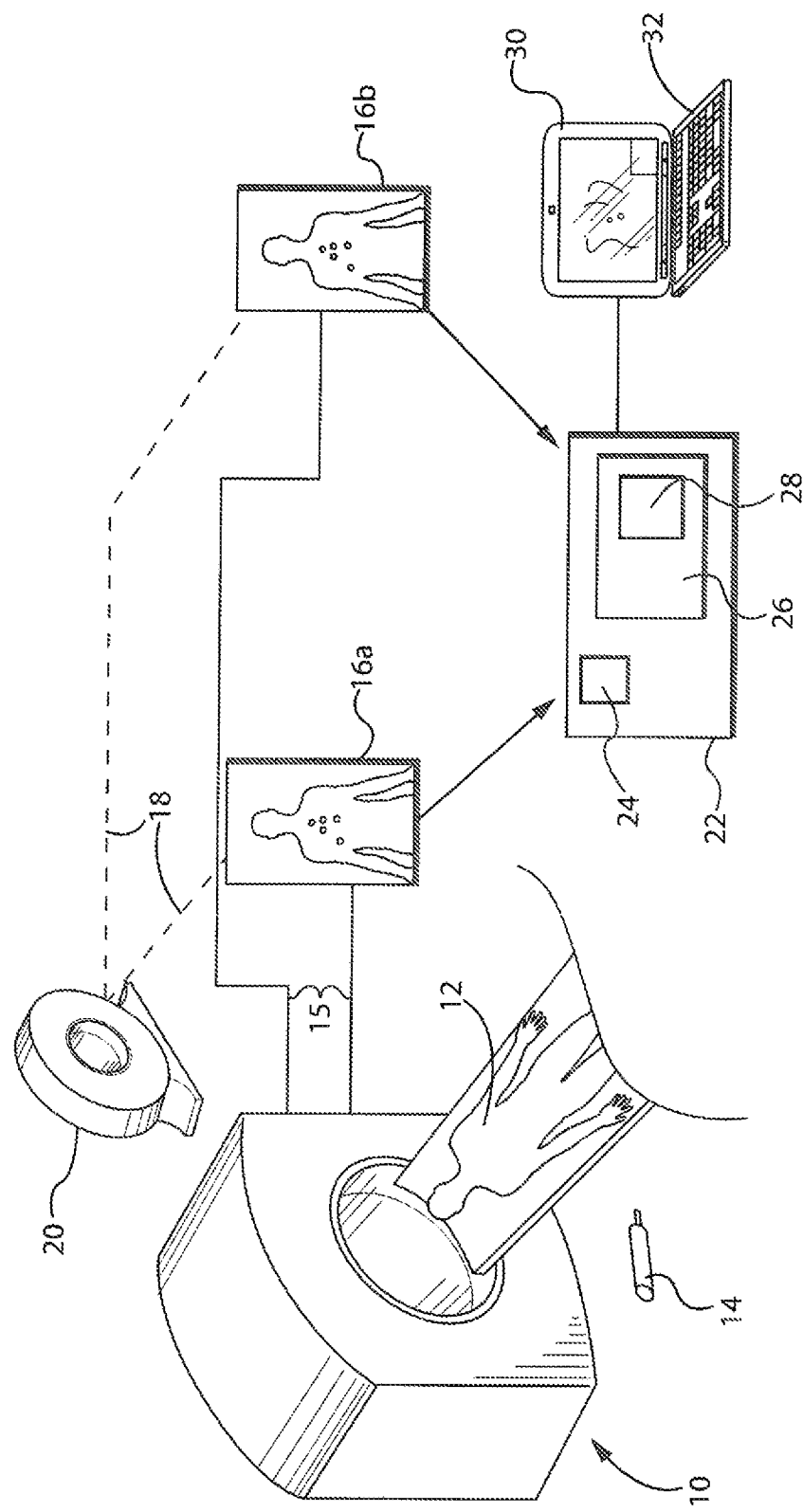
FIG. 1 is a simplified block diagram of the hardware associated with the present invention showing a scanning process for obtaining molecular (e.g., PET) and anatomical (e.g., CT) scans for use in practice of the present invention.

Referring now to FIG. 1, scanner 10 capable of molecular imaging (also termed "functional imaging" or "metabolic imaging") may scan a patient 12 after introduction of a molecular imaging agent 14 (e.g., such as a radioactive tracer) into the patient 12.

The scanner 10, in one example, may be a PET (positron emission tomography) scanner. As is generally understood in the art, PET is a nuclear medical imaging technique producing three-dimensional image data revealing functional processes in the body reflected by migration of the molecular imaging agent 14 preferentially to tumor tissue. The molecular imaging agent 14 in this case will be a positron emitting radio nucleotide attached to a biologically active molecule, the latter selected to participate in the tumor's metabolism.

The patient 12 may be scanned at two different times to produce molecular imaging data 15 that may be collected into two "scans" 16a and 16b, for example, scan 16a taken before and scan 16b taken after a session of treatment of the patient 12 by chemotherapy, radiation therapy, or the like. The scans 16 may be supplemented with additional scans other scanners 20, for example a conventional kilovoltage or megavoltage CT (computed tomography), MRI (magnetic resonance imaging), or ultrasound system, such as may provide higher resolution image data 18 that are presenting anatomical information typically without the metabolic information. Generally, the scans 16 will present dimensions of information associated with volume elements (voxels) distributed in three dimensions, although only two dimensions are shown for clarity.

The pre-treatment and post-treatment scans 16 may be received by an electronic computer 22 for processing as will be described in greater detail below. Generally, the electronic computer 22 includes one or more processing units 24 communicating with a memory 26 holding data and a stored program 28 for effecting portions of the present invention. The computer 22 may communicate with a graphics display 30 for displaying color output images based on the scans 16 and with user input devices 32 such as a keyboard, mouse or the like, each allowing entry of data by user. Generally, the program display 30 will display an output indicating cancer progression or regression based on measures of radiotracer uptake within multiple tumor locations in the patient 12. These measures may be based on one or both scans 16.

Program Operation

Figure 2:
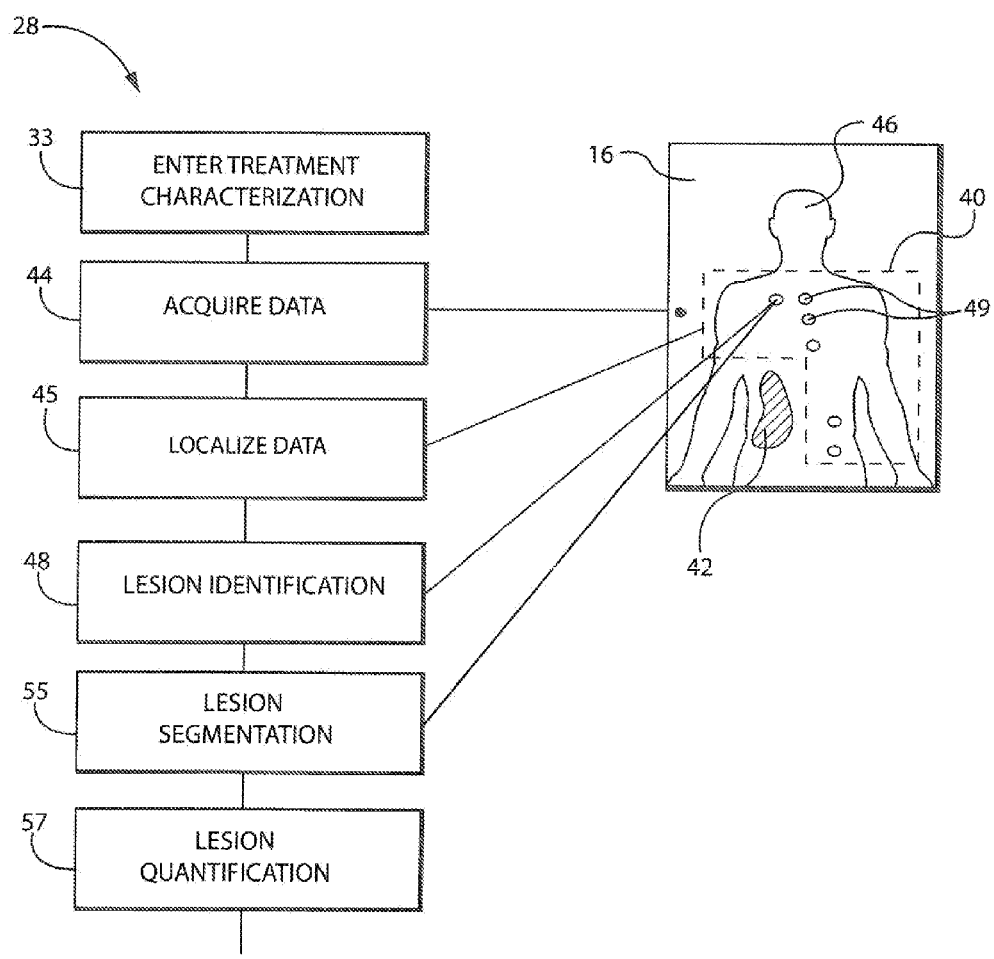
FIG. 2 is a flowchart showing principal steps in providing a quantitative measure of multiple dispersed tumor regions throughout the body of the patient.

Referring now also to FIG. 2, program 28 may accept through input device 32 information characterizing the type of cancer or other disease (such as osteoporosis) being treated and the type of molecular imaging agent 14 being used, as indicated by process block 33. For example, the type of cancer information 34 may indicate that the type of cancer is a solid tumor cancer, such as a lung cancer, or a systemic cancer such as lymphoma. This information will allow the identification of certain anatomical areas where the lesions are likely located and/or other anatomical areas where lesions are not likely to be located or else automatic identification is likely to be in error. The type of molecular imaging agent information (e.g., pharmacokinetic information) 36 may further identify incidental areas where the agent may accumulate other than lesions, for example in the liver. Examples of types of an agent 14 include FLT (3'-deoxy-3'-[$^{18}$F]fluoro-L-thymidine), a marker of cellular proliferation that quickly accumulates in proliferating cells that are synthesizing DNA and can be imaged with PET, NaF (a bone seeker) which is usually chosen for imaging of treatment response in metastatic bone lesions, and can be imaged with PET, and [$^{18}$F]Galacto-RGD (an $\alpha v \beta 3$-selective tracer) which is used as an imaging agent for anti-angiogenic therapy since the integrin $\alpha v \beta 3$ plays a key role in angiogenesis and can be imaged with PET.

A database 38 implemented and managed by the program 28 may link particular types of cancer information 34 and types of radiotracer information 36 to a set of anatomical regions 40 defining volumes of tissue associated with particular organs or body structures. A particular region 40 may, for example, be such as to exclude an organ 42 such as the liver which may tend to accumulate the radiotracer despite lack of lesions. Some regions 40, for example, may concentrate on bones or other regions on particular organs or tissue types. This database 38 may be prepared by experts and may be refined by empirical experience and describe these regions 40 geometrically with respect to known fiducial points in the images for automatic or semiautomatic placement (e.g., using anatomical atlases).

At process block 44, data from a molecular imaging scan 16 may be received. This data will typically be acquired on a separate scanner 10 but conceivably could be done on an integrated system where computer 22 is part of the control system for the scanner 10. The scan 16 provides a set of data points 46 representing molecular imaging agent uptake at three dimensionally dispersed voxels throughout the patient 12 to identify an agent uptake to specific tissue locations. As noted, the scan 16 may be augmented with higher resolution anatomical data from another imaging modality registered with the molecular imaging information using known techniques.

Upon receipt of the molecular imaging scan 16, the previously identified regions 40 may be applied to the scan data using fiducial points in the scans 16 or other registration techniques to localize the lesions that will be identified per process block 45.

Figure 3:
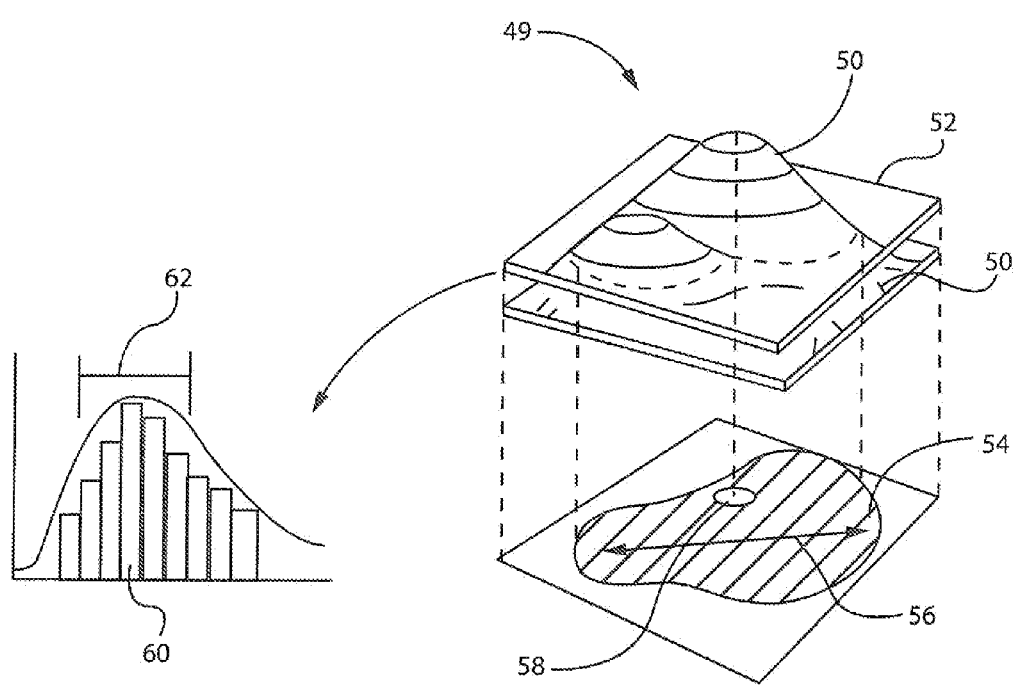
FIG. 3 is a simplified diagram of a measure of a molecular imaging agent uptake in the region of a lesion showing features used for lesion identification and characterization and as a basis for measures of that lesion.

Referring now to FIG. 3, the scan 16a represents the distribution of the molecular imaging agent uptake through the body 50 (represented as a third upward dimension to a two-dimensional slice through the three-dimensional scan data). As is generally understood in the art, intensity values for each voxel generally reflect the actual agent concentration at the voxel compared or normalized to an expected agent concentration 14 evenly distributed throughout the whole body of the patient 12.

The regions 40 define the volume of tissue in which lesions will be identified at succeeding process block 48. By eliminating some tissue, and especially tissue that may indicate false positive uptakes, a more sensitive assessment of tumor progress may be made when multiple diffuse tumors may be present.

One method of identifying lesions may evaluate the molecular imaging uptake values within the regions 40 against a threshold 52, for example 0.5, of just above background. Voxels of the patient 12 having the molecular imaging agent uptake values 50 above the threshold 52 may then be identified as lesions 49. Other identification techniques are contemplated including, for example, manual contouring in which an image analyst freehand contours colored molecular imaging data using a CT image as a guide when necessary, or circular contouring where an experienced physician adjusts the size of the circle around each tumor, or other automatic contouring techniques, such as uptake gradient based methods, or imaging feature-identifying methods.

The identified volume 54 may be then segmented as indicated by process block 55 using various morphometric filters or the like to refine the edges of the volume 54, for example, by smoothing, shrinking, or dilating that volume. This segmentation process may consider the particular anatomical regions in which a lesion is found, for example, to enforce a minimum lesion size or the like. Upon completion of the segmentation process, a lesion 49 volume and location is recorded together with its anatomical location.

Once the segmentation is complete, a measure of the lesion is made as indicated by process block 57 to provide a quantified value reflecting the molecular imaging agent uptake for that particular lesion 49. This segmentation provides a lesion volume 54 (represented as a two-dimensional area in the figures) that may be characterized in a number of ways.

A first set of characterizations may deal with the shape and size of the volume 54, for example, measuring the largest dimension 56 of the lesion 49 or the total volume of the lesion 49.

A second set of measures may characterize the uptake values within the volume 54 of the lesion 49, for example, identifying a maximum value 58 being the largest uptake value 50 in the volume 54, a peak uptake value 50 being the average uptake value 50 in a small region holding the maximum, a mean value being an average of uptake values within the volume 54, a total value being the integral of the uptake values 50 taken over the volume 54 and an average uptake value along an iso-contour of the volume 54 that is a given percentage of the uptake maximum. Other such measures may also be used and are contemplated by the present invention.

A third set of measures that may characterize a lesion 49 are those that indicate a distribution of molecular imaging uptake values 50 within volume 54. For example, each uptake value for a voxel within the volume 54 may be collected in a histogram 60 whose horizontal axis indicates the uptake value and whose vertical axis indicates number of voxels having that value. The heterogeneity or spread of the uptake distribution presented by the histogram 60 may be quantified by a coefficient of variation 62 (CV) which is the standard deviation of the distribution of the histogram 60 normalized by the mean uptake value, or other heterogeneity measures, such as average intensity correlation distance, which is an average distance of the uptake values of similar value.

A fourth set of measures may evaluate the distribution (e.g. heterogeneity) of the molecular imaging uptake values 50 in the entire body and/or the integrated value of the molecular imaging uptake values 50 in the entire body.

When only a single scan 16 is considered, any of these measures may be reported out for each of the identified lesions 49 and/or a combined value of the measures of each of the identified lesions 49 may be output. This combined value may be, for example, a simple average measure taken over all lesions 49 or such an average where the measure of each lesion is weighted by the size of the lesion 49. Alternatively, for example, for measures such as the measure of the maximum uptake in each lesion 49, a maximum of these measures may be reported. Different or multiple measurements may be reported as selected by the user.

Figure 4:
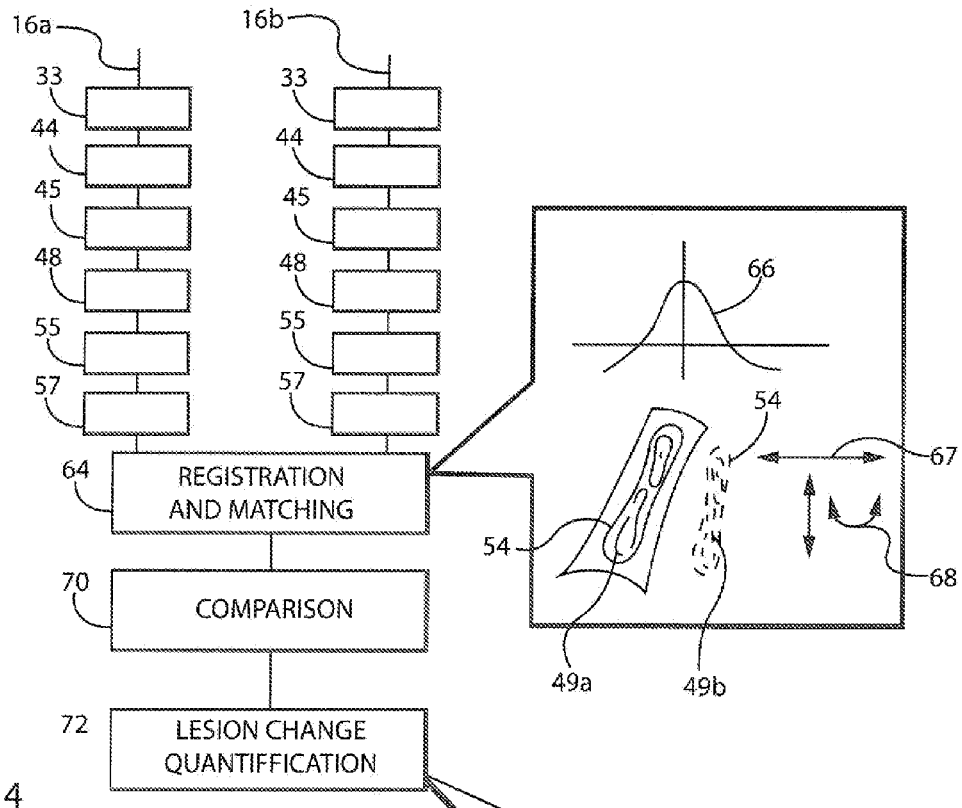
FIG. 4 is a flowchart incorporating the steps of FIG. 2 for both a pre-treatment and post-treatment scan showing registration of lesion volumes between the scans and the production of comparative measures.
Figure 5:
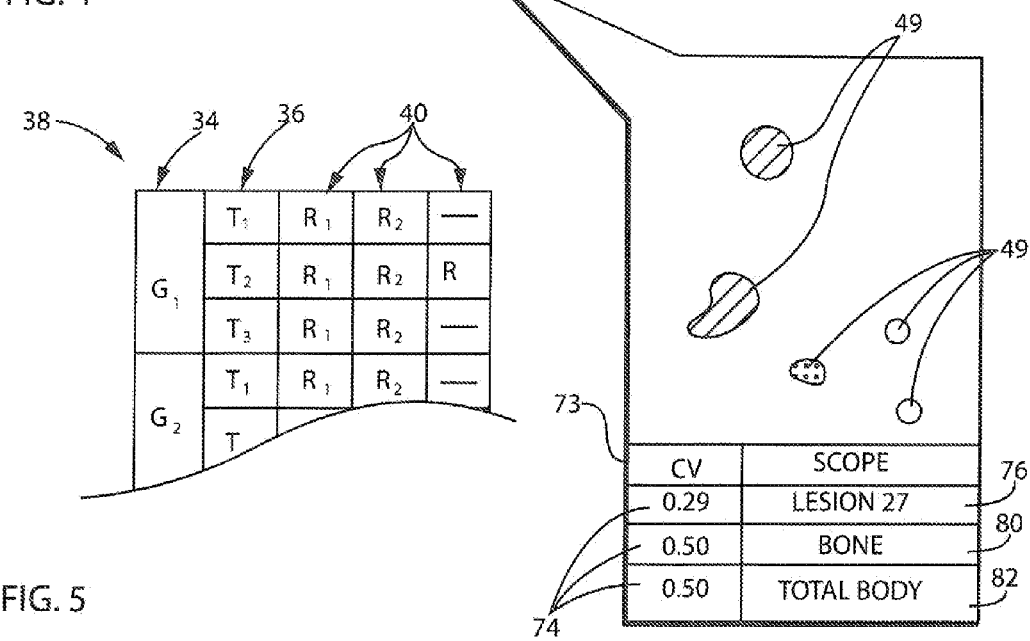
FIG. 5 is a simplified representation of an anatomical regions database of the type that may be used with the present invention.

Referring now to FIG. 4, in an alternative embodiment, these measures may be cast as differences between corresponding lesions 49 in a pretreatment scan 16a as compared to a post treatment scan 16b. It will be recognized that the treatment may be fractionated so that multiple pre- and post-treatment scans may be obtained where one post-treatment scan becomes a pre-treatment scan for a later scan; these terms are only relative.

In this technique, the processes of process blocks 33, 44, 45, 48, 55, and 57 may be performed for each of the scans 16a and 16b. At process block 64, the multiple, localized, identified, segmented and quantified lesions 49 in each scan 16 are matched and registered with each other. This matching and registration allows not simply a comparison of the overall measures for each lesion 49 (which would require only a matching and not a registration) but allows measures that require a voxel by voxel comparison between the volumes of the lesions 49. For example, a distribution of a histogram formed of differences between corresponding voxels could be created. The registration process also allows identical regions of interest to be defined on both scan 16a and 16b (for example taking the largest, smallest or union of the two volumes 54) eliminating variations in volume-based measurements caused by slightly different volume determinations. Note that the registration may make use of one or both of the data 15 from the scanner 10 and image data 18 of other scanners 20.

Referring still to FIG. 4, in one example registration process may mathematically "slide" data of volume 54 of lesion 49a (for example in marrow of a bone) in the pre-treatments scan 16a with respect to the data of volume 54 of lesion 49b in the post-treatment scan 16b to measure a correlation 66 between the values of those volumes (e.g. molecular imaging agent uptake, or other modality data). This sliding process may be conducted in multiple dimensions, for example vertically and horizontally, as indicated by arrows 67 (and also in depth not visible in the figures), in multiple dimensions of rotation as represented by arrow 68, including accounting for potential deformations between the scans, until a best match is obtained. The ability to correlate in rotation and deformation is particularly helpful in matching tumors in limbs and easy deformable tissues to accommodate the bending of limbs or deformation of tissue of the patient 12 between scans 16. For this purpose the rotation and deformation may be constrained to reflect possible movement of the particular limb, or tissue plasticity related to the identified anatomical regions and conditioned by mechanical properties of the particular tissue. The matching process may simply select tumors that are closest together in the pre- and post-scan images before or after registration and/or may look at relative size and shape of the minors.

At process block 70, a comparison between the overall values of each measure of the lesions 49a and 49b may be made and at process block 72 measures of changes in these measures may be quantified and displayed, for example, on display 30 of FIG. 1. One possible graphic display of this data of the regions of the lesion 49, for example, shows the locations of each lesion 49 colored to show whether there has been a good response (e.g. shaded green), a poor response (e.g. shaded red) or whether the lesion is new (e.g. shaded yellow). This graphic representation may be accompanied by a quantitative table 73 listing particular measures 74 of individual lesions 49 each assigned to a lesion identification number 76, for example, determined by selecting a graphic representation of the lesion 49. The measures 74 may, in addition, be aggregated measures for lesions in a particular anatomical region 40 indicated by a caption 80 in the table 73, or may present a combined total of the compared assessment of all lesions with respect to the total body indicated by a caption 82. This combined change total may again be a simple or complex average as described above.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including

What we claim is:

1. A method of assessing treatment of a patient comprising the steps of:
   acquiring a first scan of a molecular imaging agent uptake of tissue of the patient, the molecular imaging agent uptake identifying diseased tissue;
   processing the first scan using an electronic computer executing a stored program to:
   (a) receive an input describing at least one of disease type and molecular imaging agent type;
   (b) process the input to produce a set of anatomical regions of interest based on the input, the anatomical regions of interest representing a subset of a region of the first scan;
   (c) identify multiple disease locations within the anatomical regions based on molecular imaging agent uptake indicated by the first scan;
   acquiring a second scan of molecular imaging agent uptake of the tissue of the patient at a later time and repeating steps (a)-(c) for this second scan;
   matching corresponding disease locations between the first and second scans by rotating and shifting the disease locations independently into alignment with each other;
   measuring a change between corresponding disease locations; and
   providing an output fir a measure indicating the change in corresponding disease locations.

2. The method of claim 1 further including the step of outputting an assessment of disease heterogeneity based on characterization of the molecular imaging agent uptake of the whole patient.

3. The method of claim 1 further including the step of outputting measures of molecular imaging agent uptake of individual subsets of the multiple disease locations.

4. The method of claim 1 further including the step of outputting an assessment of disease burden based on an integrated measure of molecular imaging agent uptake over the whole patient.

5. The method of claim 2 wherein the measures of molecular imaging agent uptake of subsets are divided in the output according to anatomical categories of disease locations of the subsets.

6. The method of claim 1 further including a segmentation defining boundaries around disease locations after the identification.

7. The method of claim 1 wherein the anatomical regions are those of bone, bone lesions or bone marrow and wherein the independent registration matches bones, bone lesions, or bone marrow between corresponding bones in the scans rotated and shifted independently into alignment with each other.

8. The method of claim 1 wherein the output includes a graphic display of the tissue showing measures for different disease locations color coded according to response between the scans.

9. The method of claim 1 wherein the measures are selected from the group of imaging measures consisting of: uptake mean, uptake maximum, uptake peak, uptake total, uptake coefficient of variation, lesion volume, lesion linear dimension, and combinations of the above.

10. The method of claim 1 wherein the first and second scans are molecular imaging scans and further including the step of acquiring first and second anatomical scans of the tissue of the patient and processing the first and second anatomical scans and the input to produce the set of anatomical regions of interest.

11. An apparatus for assessing cancer treatment of a patient comprising:
    an electronic computer executing a stored program to
    (a) receive a first scan of molecular imaging agent uptake of tissue of the patient, the molecular imaging agent identifying disease tissue;
    (b) receive an input describing at least one of cancer type and molecular imaging agent type;
    (c) process the input to produce a set of anatomical regions of interest based on the input, the anatomical regions of interest representing a subset of a region of the first scan;
    (d) identify multiple disease locations within the anatomical regions based on molecular imaging agent uptake indicated by the first scan;
    (e) receive a second scan of molecular imaging agent uptake of the tissue of the patient at a later time and repeating steps (b)-(d) for this second scan;
    (f) match corresponding disease locations between the first and second scans by rotating and shifting the disease locations independently into alignment with each other;
    (g) measure a change in corresponding disease locations; and
    (h) provide an output for a measure indicating the change in corresponding disease locations.

12. The apparatus of claim 11 wherein the output provides measures of molecular imaging agent uptake of individual subsets of the multiple disease locations.

13. The apparatus of claim 12 wherein the measures of molecular imaging agent uptake of subsets are divided in the output according to anatomical categories of disease locations of the subsets.

14. The apparatus of claim 11 further including a segmentation defining boundaries around the disease locations after the identification.

15. The apparatus of claim 11 wherein the anatomical regions are those of bone, bone lesions, or bone marrow and wherein the independent registration matches at least one of: bone, bone lesions and bone marrow between corresponding bones in the scans rotated and shifted independently into alignment with each other.

16. The apparatus of claim 11 wherein the output provides a graphic display of the tissue showing measures for different disease locations color coded according to response between the scans.

17. The apparatus of claim 11, wherein the measures are selected from the group of imaging measures consisting of: uptake mean, uptake maximum, uptake peak, uptake total, uptake coefficient of variation, lesion volume, lesion linear dimension, and combinations of the above.

18. The apparatus of claim 11 wherein the first and second scans are molecular imaging scans and further including processing first and second anatomical scans of the patient and the input to produce the set of anatomical regions of interest.

* * * * *